United States Patent
Koutnik et al.

(10) Patent No.: US 11,452,704 B2
(45) Date of Patent: Sep. 27, 2022

(54) PREVENTION AND TREATMENT OF MUSCLE WASTING WITH KETONE SUPPLEMENTATION

(71) Applicant: UNIVERSITY OF SOUTH FLORIDA, Tampa, FL (US)

(72) Inventors: Andrew Paul Koutnik, Tampa, FL (US); Dominic Paul D'Agostino, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/768,242

(22) PCT Filed: Nov. 30, 2018

(86) PCT No.: PCT/US2018/063497
§ 371 (c)(1),
(2) Date: May 29, 2020

(87) PCT Pub. No.: WO2019/109050
PCT Pub. Date: Jun. 6, 2019

(65) Prior Publication Data
US 2021/0186914 A1    Jun. 24, 2021

Related U.S. Application Data

(60) Provisional application No. 62/629,917, filed on Feb. 13, 2018, provisional application No. 62/592,842, filed on Nov. 30, 2017.

(51) Int. Cl.
| | | |
|---|---|---|
| *A61K 31/22* | (2006.01) | |
| *A61P 21/06* | (2006.01) | |
| *A61K 31/198* | (2006.01) | |
| *A61K 31/23* | (2006.01) | |
| *A61K 47/26* | (2006.01) | |

(52) U.S. Cl.
CPC ............ *A61K 31/22* (2013.01); *A61K 31/198* (2013.01); *A61K 31/23* (2013.01); *A61K 47/26* (2013.01); *A61P 21/06* (2018.01)

(58) Field of Classification Search
CPC .. A61K 31/22; A61K 2300/00; A61K 31/198; A61K 31/23; A61K 45/06; A61K 47/14; A61K 47/26; A23L 33/10; A23L 33/12; A23L 3/00; A61P 21/06
See application file for complete search history.

(56) References Cited

U.S. PATENT DOCUMENTS

| | | | |
|---|---|---|---|
| 7,507,425 B2 | 3/2009 | Rosenbloom | |
| 2010/0189816 A1 | 7/2010 | Schneid | |
| 2014/0072654 A1* | 3/2014 | D'Agostino | ......... A61K 31/121 |
| | | | 424/613 |
| 2015/0024032 A1 | 1/2015 | Tweardy et al. | |
| 2015/0065571 A1* | 3/2015 | Clarke | .................. A61K 31/22 |
| | | | 514/546 |
| 2015/0231172 A1 | 8/2015 | D'Agostino et al. | |

OTHER PUBLICATIONS

Dodson et al. (Annual Rev. Med. 2011,62, 265-79). (Year: 2011).*
International Search Report and Written Opinion in PCT/US2018/063497. dated Jan. 22, 2019. 9 pages.
Schmidt, Melanie et al. "Effects of a ketogenic diet on the quality of life in 16 patients with advanced cancer: A pilot trial". Nutrition and Metabolism. 2011. 13 pages.
Stefan D. Anker et al., Muscle wasting disease: a proposal for a new disease classification, J Cachexia Sarcopenia Muscle, 2014, 5:1-3.
Stephan Von Haehling et al., Prevalence and clinical impact of cachexia in chronic illness in Europe, USA, and Japan: facts and numbers update 2016, Journal of Cachexia, Sarcopenia and Muscle, 2016, 7:507-509.

* cited by examiner

*Primary Examiner* — Umamaheswari Ramachandran
(74) *Attorney, Agent, or Firm* — Meunier Carlin & Curfman LLC

(57) ABSTRACT

Methods and compositions for treating or preventing muscle wasting resulting from an underlying disease or disorder, such as cancer cachexia. A therapeutically effective amount of a ketogenic supplement—such as R,S 1,3 butanediol diacetoacetate, R,S 1,3-butanediol acetoacetate diester, derivatives thereof, or combinations thereof—is administered to a patient or subject in need. The ketogenic supplement may further include a medium chain triglyceride in combination with the ketone ester.

7 Claims, 9 Drawing Sheets

PREVENTION AND TREATMENT OF MUSCLE WASTING WITH KETONE SUPPLEMENTATION

CROSS REFERENCE TO RELATED APPLICATIONS

This application is a United States National Phase Patent Application filed under 35 U.S.C. § 371 of International Patent Application Number PCT/US2018/063497, filed Nov. 30, 2018, which claims the benefit of priority to U.S. Provisional Application Nos. 62/592,842, filed Nov. 30, 2017, and 62/629,917, filed Feb. 13, 2018, the disclosures of each are incorporated by reference herein in their entireties.

FIELD

The disclosed subject matter relates, generally, to muscle atrophy. More specifically, the disclosed subject matter relates to compositions and therapies for preventing or reducing muscle atrophy caused by any of a number of diseases or disorders.

BACKGROUND

Muscle is a vital organ that plays a role in maintaining homeostasis for functional movement, immune functionality, metabolism, disease and drug tolerance, etc. Muscle wasting is a serious consequence and can be the primary or secondary causes of poor outcomes in various disease states. For example, while most cancer deaths are a result of metastatic disease, about 20% directly result from cachexia. Cancer cachexia is characterized by the loss of skeletal muscle mass, with or without fat loss, that cannot be fully reversed by conventional nutritional support and results in progressive functional impairment.

Nutritional, or therapeutic, ketosis is the physiological state of elevated blood ketone body levels (typically above 0.5 mmol/L) resulting from ketogenic diets, calorie restriction, therapeutic fasting and/or supplementation with ketogenic precursors. Ketone bodies represent alternative energy substrates for both peripheral tissues and the central nervous system. The two most abundant and physiologically significant ketone bodies are acetoacetate and β-hydroxybutyrate (βHB), while the third ketone body, acetone, is produced as a byproduct that the lungs breathe off. The body produces ketone bodies during nutritional or therapeutic ketosis in the range of 2-16 mmol/L. The metabolism of ketone bodies is associated with anticonvulsant effects, enhanced brain metabolism, neuroprotective, muscle sparing properties and improvement in cognitive and physical performance. Science-based improvements in efficiency of cellular metabolism, managed through ketone supplementation, could have beneficial impacts on physical, cognitive health, psychological health, warfighter resilience and a long-term impact on health with respect to the common avoidable diseases such as obesity, neurodegenerative diseases, diabetes and cancer.

In periods of fasting, extreme exercise, and/or low carbohydrate consumption, glucose stores in the body are rapidly used and can become quickly depleted. Failure to replenish glucose stores as they become depleted causes the body to turn to an alternative method to generate energy by creating ketone bodies. Ketone bodies can be used by every cell of the body as a replacement fuel to satisfy the body's energy needs, including the needs of the brain. During a prolonged fast, for example, blood ketone levels will increase to as high as 2 or 3 mmol/L. It is conventionally understood and agreed that when blood ketones rise above 0.5 mmol/L, the heart, brain and peripheral tissues are using ketone bodies (β hydroxybutyrate and acetoacetate) as the primary fuel source. This condition is referred to as ketosis, or "nutritional ketosis." This is distinguished from, and should not be confused with, diabetic or alcoholic ketoacidosis, which is the runaway accumulation of ketone bodies and associated drop in blood pH. Diabetic ketoacidosis is associated with the absence of insulin as occurs in those suffering from type 1 diabetes. Ketoacidosis typically results in blood ketone levels in excess of 25 mmol/L in combination with metabolic derangement and electrolyte imbalance.

When in ketosis, the body primarily burns fat for fuel. This is accomplished because fat stores in the body are utilized to create the water-soluble ketone bodies beta-hydroxybutyrate (βHB) and acetoacetate (also known as acetylacetonate). These ketone bodies are then used by the body as its primary energy source. An advantage of pursuing weight loss through a ketogenic diet is that a ketogenic diet may result in loss of fat stores while maintaining and protecting muscle mass. The potential muscle sparing properties of a ketogenic diet may result in improvement in physical performance.

Notwithstanding the difficulties in achieving ketosis itself, a proven effect of ketosis or ketogenic supplementation on muscle atrophy resulting from various diseases and disorders, such as cancer cachexia, is unknown. Attempts have been made to treat cachexia and underlying diseases, examples including U.S. Patent Application Publication No. 2010/0189816; U.S. Patent Application Publication No. 2015/0024032; U.S. Patent Application Publication No. 2014/0072654; U.S. Pat. No. 7,507,425; U.S. Patent Application Publication No. 2015/0065571; and Schmidt, M., et al. (2011). Effects of a ketogenic diet on the quality of life in 16 patients with advanced cancer: A pilot trial. Nutrition & Metabolism, 8, 54. However, none are able to definitively show reduction or prevention of muscle wasting that commonly results from various diseases and disorders.

Accordingly, what is needed are therapies or compounds that mitigate muscle wasting in various diseases in order to maintain optimal health and quality of life. The compositions and methods disclosed herein address these and other needs.

SUMMARY

In accordance with the purposes of the disclosed materials and methods, as embodied and broadly described herein, the disclosed subject matter, in one aspect, relates muscle atrophy, muscle wasting, and compositions and methods for preventing or treating these conditions. In certain aspects, disclosed are methods of treating or preventing muscle wasting resulting from a disease or disorder comprising administering a therapeutically effective amount of a ketogenic supplement. In other aspects, disclosed are compositions for treating or preventing muscle wasting resulting from a disease or disorder comprising a ketogenic supplement in a pharmaceutically acceptable carrier.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

For a fuller understanding of the invention, reference should be made to the following detailed description, taken in connection with the accompanying drawings, in which.

DETAILED DESCRIPTION

Figure 1:
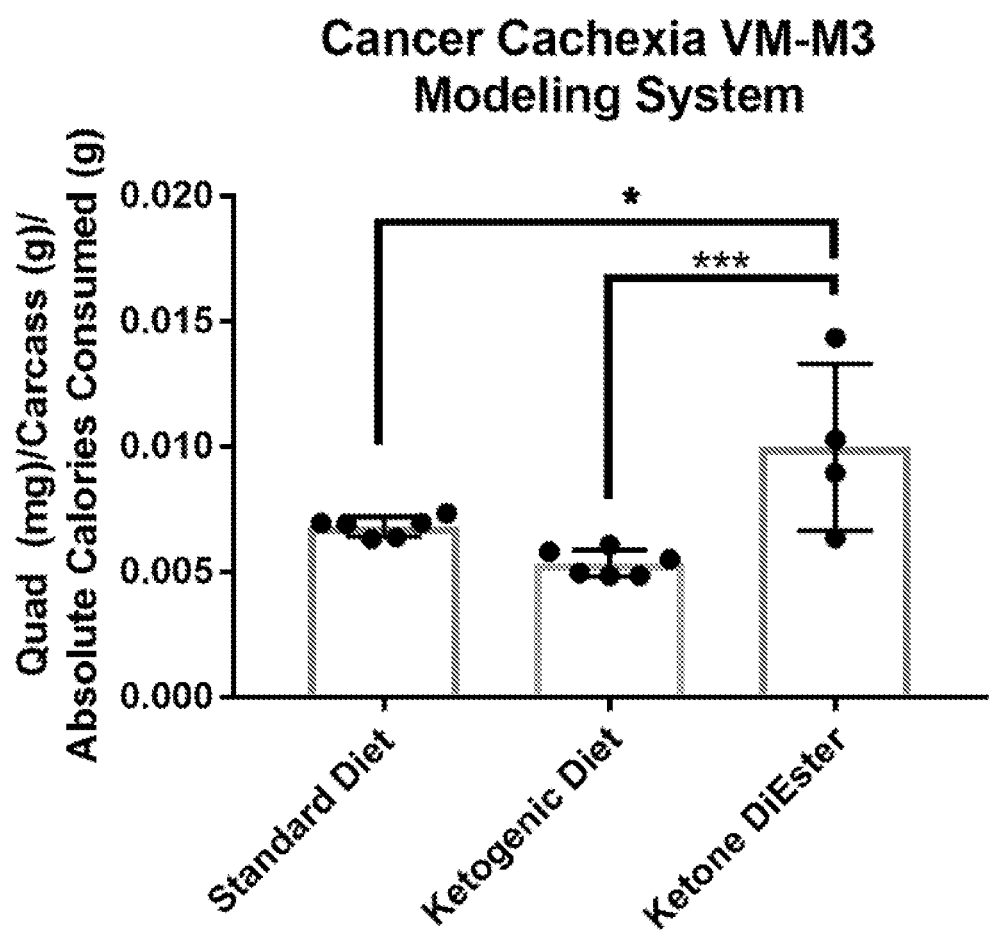
FIG. 1 depicts ratios of muscle mass to amount of calories consumed within a cancer cachexia VM-M3 modeling system, specifically with subjects having been fed standard diet, ketogenic diet, and ketone diester.

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an ingredient" includes mixtures of two or more such ingredients, reference to "the supplement" includes mixtures of two or more such supplements, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

By "reduce" or other forms of the word, such as "reducing" or "reduction," is meant lowering of an event or characteristic (e.g., muscle wasting). It is understood that this is typically in relation to some standard or expected value, in other words it is relative, but that it is not always necessary for the standard or relative value to be referred to. For example, "reduces muscle wasting" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treat", "treatment", "treating", and the like refer to acting upon a condition (e.g., muscle wasting) with an agent (e.g., ketogenic supplementation) to affect the condition by improving or altering it. The improvement or alteration may include an improvement in symptoms or an alteration in the physiologic pathways associated with the condition. The aforementioned terms cover one or more treatments of a condition in a patient (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reduction in muscle wasting or increase in muscle mass).

The term "patient" preferably refers to a human in need of prevention or treatment of muscle wasting, a patient suffering from cancer cachexia. However, the term "patient" can also refer to non-human animals, preferably mammals such as dogs, cats, horses, cows, pigs, sheep and non-human primates, among others, that are in need of prevention or treatment of muscle wasting. The term "patient" is used interchangeably with the term "subject."

As used herein, the term "composition" is intended to encompass a product comprising the specified ingredients in the specified amounts, as well as any product which results, directly or indirectly, from combination of the specified ingredients in the specified amounts.

As used herein "beta-hydroxybutyrate," also known as HB or BHB, is a carboxylic acid having the general formula $CH_3CHOHCH_2COOH$ which may be utilized by a patient's body as a fuel source during instances of low glucose levels in the patient and is considered a ketone body. In the present disclosure, salt variants of beta-hydroxybutyrate are disclosed.

"Ketosis" as used herein refers to a subject having blood ketone levels within the range of about 0.5 mmol/L and about 16 mmol/L. Ketone levels sustained above 0.5 mmol/L and ideally in the range of 1.0 to 3.0 mmol/L appear to offer the most therapeutic effects in humans. Ketosis may improve mitochondrial function, elevate Krebs cycle intermediates (e.g., succinate, fumarate), decrease ROS production, reduce or prevent muscle wasting or atrophy, reduce inflammation, elevate adenosine, and increase the activity of neurotrophic factors associated.

The term "administration" or "administering" is used to describe the process in which individual ketone esters, including R,S-1, 3-butanediol acetoacetate diester, and butanediol, R,S-1,3-butanediol, beta-hydroxybutyrate salts and/or medium chain triglycerides in any combination are delivered to a subject. The composition can be administered in various ways including oral, intragastric, and parenteral (referring to intravenous and intra-arterial and other appropriate parenteral routes), among others. Each of these conditions can be readily treated using other administration routes of R,S 1,3-butanediol acetoacetate diester, R,S 1,3 butanediol diacetoacetate, medium chain triglycerides, and/or other ketone salts or supplementation, derivatives, or any combination thereof to treat or prevent a disease or condition.

Administration will often depend upon the amount of compound administered, the number of doses, and duration of treatment. In an embodiment, multiple doses of the agent are administered. The frequency of administration of the agent can vary depending on any of a variety of factors, such as timing of treatment from previous treatments, objectives of the treatment, i.e., reduction and/or prevention of muscle waste, and the like. The duration of administration of the agent, e.g., the period of time over which the agent is administered, can vary, depending on any of a variety of factors, including patient response, desired effect of treatment, etc.

The term "therapeutically effective amount" as used herein describes concentrations or amounts of components such as agents which are effective for producing an intended result, including reduction or prevention of muscle wasting. Compositions as disclosed herein can be used to effect a favorable change in muscle mass, whether that change is an improvement, relieving to some extent one or more of the symptoms of the condition being treated, and/or that amount that will prevent, to some extent, one or more of the symptoms of the condition that the host being treated has or is at risk of developing, or a complete cure of the disease or condition treated. A therapeutically effective amount can be administered in one or more doses.

Therapeutically effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective. The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art, unless otherwise noted.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

Throughout this disclosure reference to a compound with stereocenters that does not specify a specific stereochemistry is meant to include specific reference to each enantiomer, diastereomer, mesocompound, and racemic and scalemic mixtures thereof.

Reference will now be made in detail to specific aspects of the disclosed materials, compounds, compositions, articles, and methods, examples of which are illustrated in the accompanying Examples and Figures.

Preventing muscle atrophy/wasting is critical for one's health, quality of life, and survival. As evidenced by the following studies, ketone supplementation was determined herein to be a potent anti-catabolic agent that can attenuate tissue wasting.

Compositions

Disclosed herein are compositions for treating or preventing muscle wasting resulting from a disease or disorder. The disclosed compositions can comprise a ketogenic supplement in a pharmaceutically acceptable carrier. The amount of ketogenic supplement in the disclosed compositions can be from 1% to 99% by weight of the disclosed compositions, e.g., the ketogenic supplement can be from 1, 5, 10, 15, 20, 25, 30, 35, 40, 45, 50, 55, 60, 65, 70, 75, 80, 85, 90, 95, or 99% of the composition by weight, where any of the stated values can form an upper or lower endpoint of a range. Likewise the pharmaceutically acceptable carrier can be from 1% to 99% by weight of the disclosed compositions, e.g., the pharmaceutically acceptable carrier can be from 1, 5, 10, 15, 20, 25, 30, 35, 40, 45, 50, 55, 60, 65, 70, 75, 80, 85, 90, 95, or 99% of the composition by weight, where any of the stated values can form an upper or lower endpoint of a range.

In other examples, the ketogenic supplement can be one or more compounds chosen from acetoacetate, 1,3-butanediol, 1,3-butanediol acetoacetate monoester, 1,3-butanediol acetoacetate diester, or any combination thereof. In a specific example, the ketogenic supplement is R,S-1,3-butanediol diacetoacetate or a derivative thereof. In specific examples the ketogenic supplement is R,S-1,3-butandiol, R,S-1,3-butanediol acetoacetate diester, or a combination of the two. The amount of these ketogenic supplements in the disclosed compositions can be at least 0.001 g, e.g., from 0.001 g to 300 g, e.g., 0.001, 0.005. 0.01. 0.05, 0.1, 0.5, 1, 10, 20, 30, 40, 50, 60, 70, 80, 90, or 100 g, 200 g, 300 g where any of the stated values can form an upper or lower endpoint of a range. Further, the amount of ketogenic supplement in the disclosed compositions can be an amount sufficient to provide from 0.5 g to 300 g, from 1 g to 40 g, from 5 g to 30 g, or from 10 g to 20 g of ketogenic supplement to a patient. In other examples, the ketogenic supplement can be present in the composition at 0.5 g, 1 g, 2 g, 4 g, 5 g, 6 g, 7 g, 8 g, 9 g, 10 g, 11 g, 12 g, 13 g, 14 g, 15 g, 17 g, 19 g, 20 g, 22 g, 24 g, 26 g, 28 g, 30 g, 32 g, 34 g, 36 g, 38 g, 40 g, 42 g, 44 g, 46 g, 48 g, 50 g, 52 g, 54 g, 56 g, 58 g, 60 g, 62 g, 64 g, 66 g, 68 g, 70 g, 72 g, 74 g, 76 g, 78 g, 80 g, 82 g, 84 g, 86 g, 88 g, 90 g, 92 g, 94 g, 96 g, 98 g, 100 g, 200 g, 300 g. Alternatively, the ketogenic supplement can be present in the composition in an amount sufficient to provide from 0.001 g to 20 g per kg of patient, or from 5 g to 10 g per kg of patient.

In specific examples, the ketone supplement does not contain a beta-hydroxybutyrate, a monoester of beta-hydroxybutyrate, or glycerol.

In further examples, the ketogenic supplement further includes a medium chain triglyceride (MGTs), monoglycerides, diglycerides, alkyl esters, or free acids thereof. Non-limiting examples and sources of the medium chain triglycerides include coconut oil, coconut milk powder, fractionated coconut oil, palm oil, palm kernel oil, triglycerides of caproic acid, triglycerides of caprylic acid, triglycerides of capric acid, and any combination thereof. The amount of these MGTs in the disclosed compositions can be from 0.001 g to 100 g, e.g., 0.5, 1, 10, 20, 30, 40, 50, 60, 70, 80, 90, or 100 g, 200 g, 300 g where any of the stated values can form an upper or lower endpoint of a range. Further, the amount of MGTs in the disclosed compositions can be an amount sufficient to provide from 0.001 g to 300 g, from 1 g to 40 g, from 5 g to 30 g, or from 10 g to 20 g of ketogenic supplement to a patient. In other examples, the MGTs can be present in the composition at 0.001, 0.005. 0.01. 0.05, 0.1, 0.5 g, 1 g, 2 g, 4 g, 5 g, 6 g, 7 g, 8 g, 9 g, 10 g, 11 g, 12 g, 13 g, 14 g, 15 g, 17 g, 19 g, 20 g, 22 g, 24 g, 26 g, 28 g, 30 g, 32 g, 34 g, 36 g, 38 g, 40 g, 42 g, 44 g, 46 g, 48 g, or 50 g, 52 g, 54 g, 56 g, 58 g, 60 g, 62 g, 64 g, 66 g, 68 g, 70 g, 72 g, 74 g, 76 g, 78 g, 80 g, 82 g, 84 g, 86 g, 88 g, 90 g, 92 g, 94 g, 96 g, 98 g, 100 g, 200 g, 300 g. Alternatively, the MGTs can be present in the composition in an amount sufficient to provide from 0.001 g to 20 g per kg of patient, or from 5 g to 10 g per kg of patient.

The ketogenic supplements disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the ketogenic supplement is combined with a pharmaceutically acceptable carrier in order to facilitate effective administration of the compound. The resulting compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also include conventional pharmaceutically-acceptable carriers, which are known to those skilled in the art. Examples of carriers for use with the disclosed compositions compounds include water, milk, juice, ethanol, dimethyl sulfoxide, glycerol, alumina, starch, saline, and equivalent carriers.

In a specific example, the disclosed compositions comprise a ketogenic supplement (e.g., R,S 1,3-butanediol acetoacetate diester, MGTs, or combinations thereof) and a liquid pharmaceutical carrier, such as water, fruit juice, or milk.

The compositions disclosed herein can further comprises additional vitamins (e.g., Vitamin A, Vitamin B6, Vitamin B12, Vitamin C, Vitamin D, Vitamin E) and/or minerals (e.g., potassium, calcium, magnesium, chromium, selenium), proteins, essential amino acids, branch chain amino acids, amino acids, or derivatives, which can be co-administered with ketone supplementation.

In further examples, disclosed herein are foodstuffs that comprise a ketogenic supplement. For example, disclosed are snack foods, nutritional bars, protein bars, beverages that comprise a ketogenic supplement (e.g., R,S 1,3-butanediol acetoacetate diester, MGTs, or combinations thereof).

Ketone Diester can be composed with protein, amino acids, or derivative of these combinations.

Methods

Also disclosed herein are methods of treating or preventing muscle wasting resulting from a disease or disorder comprising administering a therapeutically effective amount of a ketogenic supplement. The ketogenic supplement can be one or more compounds chosen from acetoacetate, 1,3-butanediol, 1,3-butanediol acetoacetate monoester, 1,3-butanediol acetoacetate diester, or any combination thereof. In a specific example, the ketogenic supplement is R,S-1,3-butanediol diacetoacetate or a derivative thereof. In specific examples the ketogenic supplement is R,S-1,3-butandiol, R,S-1,3-butanediol acetoacetate diester, or a combination of the two. These ketogenic supplements can be administered in any amount, e.g., at least 0.001 g. For example, the ketogenic supplement can be administered in an amount from 0.001 g to 300 g, e.g., 0.001 g, e.g., from 0.001 g to 300 g, e.g., 0.001, 0.005. 0.01. 0.05, 0.1, 0.5, 1, 10, 20, 30, 40, 50, 60, 70, 80, 90, or 100 g, 200 g, 300 g, where any of the stated values can form an upper or lower endpoint of a range. Further, the amount of ketogenic supplement in the disclosed compositions can be administered in an amount sufficient to provide from 0.001 g to 300 g, from 1 g to 40 g, from 5 g to 30 g, or from 10 g to 20 g of ketogenic supplement to a patient. In other examples, the ketogenic supplement can be administered at 0.001, 0.005. 0.01. 0.05, 0.1, 0.5 g, 1 g, 2 g, 4 g, 5 g, 6 g, 7 g, 8 g, 9 g, 10 g, 11 g, 12 g, 13 g, 14 g, 15 g, 17 g, 19 g, 20 g, 22 g, 24 g, 26 g, 28 g, 30 g, 32 g, 34 g, 36 g, 38 g, 40 g, 42 g, 44 g, 46 g, 48 g, or 50 g, 52 g, 54 g, 56 g, 58 g, 60 g, 62 g, 64 g, 66 g, 68 g, 70 g, 72 g, 74 g, 76 g, 78 g, 80 g, 82 g, 84 g, 86 g, 88 g, 90 g, 92 g, 94 g, 96 g, 98 g, 100 g, 200 g, 300 g. Alternatively, the ketogenic supplement can be administered in the composition in an amount sufficient to provide from 0.001 g to 20 g per kg of patient, or from 5 g to 10 g per kg of patient.

In the disclosed methods the ketogenic supplement can be administered in an amount sufficient to provide a circulating level of hydroxybutyrate and acetoacetate in the blood from 0.1 to 20 mM, preferably 0.5 to 10 mM and optimally from 1 to 8 mM for example from 2 to 5 mM, wherein at least one dose comprises a ketogenic supplement in an amount of at least 0.1 g/kg bodyweight of the patient per dose and preferably from 0.3 to 1.5 g/kg for example at least 0.3 to 0.75 g/kg bodyweight.

In the disclosed methods, the methods can further comprise the administration of a medium chain triglyceride. Non-limiting examples and sources of the medium chain triglycerides include coconut oil, coconut milk powder, fractionated coconut oil, palm oil, palm kernel oil, triglycerides of caproic acid, triglycerides of caprylic acid, triglycerides of capric acid, and any combination thereof. The amount of these MGTs that can be administered can be from 0.001 g to 300 g, e.g., 0.001 g, e.g., from 0.001 g to 300 g, e.g., 0.001, 0.005. 0.01. 0.05, 0.1, 0.5, 1, 10, 20, 30, 40, 50, 60, 70, 80, 90, or 100 g, 200 g, 300 g, where any of the stated values can form an upper or lower endpoint of a range. Further, the amount of MGTs that can be administered can be an amount sufficient to provide from 0.5 g to 50 g, from 1 g to 40 g, from 5 g to 30 g, or from 10 g to 20 g of ketogenic supplement to a patient. In other examples, the MGTs can be administered at 0.001, 0.005. 0.01. 0.05, 0.1, 0.5 g, 1 g, 2 g, 4 g, 5 g, 6 g, 7 g, 8 g, 9 g, 10 g, 11 g, 12 g, 13 g, 14 g, 15 g, 17 g, 19 g, 20 g, 22 g, 24 g, 26 g, 28 g, 30 g, 32 g, 34 g, 36 g, 38 g, 40 g, 42 g, 44 g, 46 g, 48 g, or 50 g, 52 g, 54 g, 56 g, 58 g, 60 g, 62 g, 64 g, 66 g, 68 g, 70 g, 72 g, 74 g, 76 g, 78 g, 80 g, 82 g, 84 g, 86 g, 88 g, 90 g, 92 g, 94 g, 96 g, 98 g, 100 g, 200 g, 300 g. Alternatively, the MGTs can be administered at from 1 g to 20 g per kg of patient, or from 5 g to 10 g per kg of patient.

In the disclosed methods, the ketogenic supplement can be administered on a regimen of 1 to 6 times per day, such as once or twice per day. This dosing regimen can be adjusted to provide the optimal therapeutic response. Ketogenic supplement can be administered prior, during or post to disease or disorder initiation, or independent of disease or disorder state. Ketone supplements can be administered topically. It can be co-administered with glucose, fructose, sucralose, galactose or derivative thereof, or protein, essential amino acids, branch chain amino acids, amino acids, derivatives thereof.

In any of the disclosed methods herein the ketogenic supplement can be administered with a stand diet, e.g., without restrictions as to glucose intake.

In the disclosed methods, the disease or disorder to be treated or prevented can be cachexia, cancer cachexia, inflammation-induced wasting or sepsis, sarcopenia, disuse atrophy, denervation, amyotrophic lateral sclerosis, HIV/AIDS, aging, infection, low gravity environment, chronic bedrest, immobility, amongst others. In further examples, the disorder to be treated or prevented can be voluntary or involuntary caloric restriction, anorexia, fasting, starvation, exercise/activity-induced catabolism, and elevated energy expenditure, amongst others.

In a specific aspect the disease or disorder can be cancer cachexia caused by bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Further examples of cancers treatable by the compounds and compositions described herein include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

In specific examples, the disclosed ketone supplements can be administered topically to a patient to reduce or treat muscle wasting.

In further examples, the patient is administered the ketone supplement when on a standard diet, on voluntary or involuntary caloric restriction, anorexia, fasting, starvation, or exercise/activity-induced catabolism.

Manufacture of a Medicament

Also disclosed herein are methods for the manufacture of a medicament for treating or preventing muscle wasting combining a therapeutically effective amount of a disclosed compound or product of a disclosed method with a pharmaceutically acceptable carrier or diluent.

Also disclosed herein are methods for manufacturing a medicament associated with treating or preventing muscle wasting or the need to treat or prevent muscle wasting with a pharmaceutically acceptable carrier or diluent.

In some examples, the medicament comprises a disclosed compound.

Kits

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more ketogenic supplements. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Also disclosed herein are kits comprising one or more of the disclosed compounds, and one or more of: a) at least one anticancer compound, b) instructions for treating a disorder associated with cancer, or c) instructions for treating cancer.

In some examples, the kit further comprises at least one agent, wherein the compound and the agent are co-formulated.

In some examples, the ketogenic supplements are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

There are many models of cancer cachexia, but none are ideal as they do not address all aspects of this multifaceted syndrome. The VM-M3 model is a syngeneic mouse model derived from VM-M3 cell line which, when implanted subcutaneously, results in rapid and systemic metastasis throughout the body, including to the liver, lungs, brain, kidneys, and spleen. The VM-M3 male and female model of systemic metastasis were assessed for cancer cachexia phenotype. Tumor progression, organ metastasis, skeletal muscle and adipose tissue recomposition, systemic inflammation, anorexia, albumin, blood urea nitrogen, and other clinical metabolites were evaluated. VM-M3 male and female models both present rapid systemic metastasis (31 and 32-day mean survival) with similar progressive increases in primary tumor weight in males and females, respectively.

A progressive decrease in calf skeletal muscle weight was seen from week 2 (10% and 12% reduction) to end of life (19% and 23%), with a 40% and 26% reduction in quadriceps weight at end of life for males and females, respectively. A progressive decrease in intraperitoneal white adipose tissue was seen from 20% and 20% reduction at week 2, to 82% and 100% reduction at end of life for males and females, respectively. Prolonged systemic inflammation was identified via elevated spleen weight (9- and 10-fold increase, respectively), elevated white blood cells counts, and elevated TNF-α and IL-6 at week 2 and end of life. Male and female VM-M3's also presented anorexia, hypoalbuminemia, elevated blood urea nitrogen, and reduced total protein. Dietary interventions were developed to treat this multifaceted model of metastasis induced cancer cachexia. Ketogenic diet and synthetic ketogenic agent (R,S 1,3-butanediol acetoacetate diester) were administered via diet to assess these nutritional interventions' ability to attenuate cachexic syndromes of altered tumor progression, skeletal muscle, adipose tissue, systemic inflammation, and additional cachexic biomarkers.

Example 2

Taking a model system of cancer induced tissue wasting (muscle and fat), R,S 1,3 butanediol diacetoacetate+standard diet, ketogenic diet, and standard diet were applied. VM/Dk animals were matched for sex, age, and bodyweight to ensure controlled groups. Animals were implanted with VM-M3 cell in the left flank to create the VM-M3 model of metastatic cancer. Once implanted, primary tumor forms at site of implantation, and then cells metastasize to all major organ systems that results in tissue wasting. Animals were harvested at 21 days post-cancer implantation to evaluate tissue wasting. Calculations were made to determine the percentage of muscle mass present in all groups as a ratio of total calories consumed (Quad/Carcass/Absolute calories consumed) to determine if R,S 1,3 butanediol diacetoacetate is a more potent calorie-per-calorie anti-catabolic than just a standard diet or ketogenic diet. As can be seen in FIG. 1, animals within the R,S 1,3 butanediol diacetoacetate+standard diet group had substantially higher percentage of muscle mass compared to the amount of calories consumed.

This confirms that R,S 1,3 butanediol diacetoacetate is an anti-catabolic/anti-tissue wasting compound.

Example 3

Figure 2A:
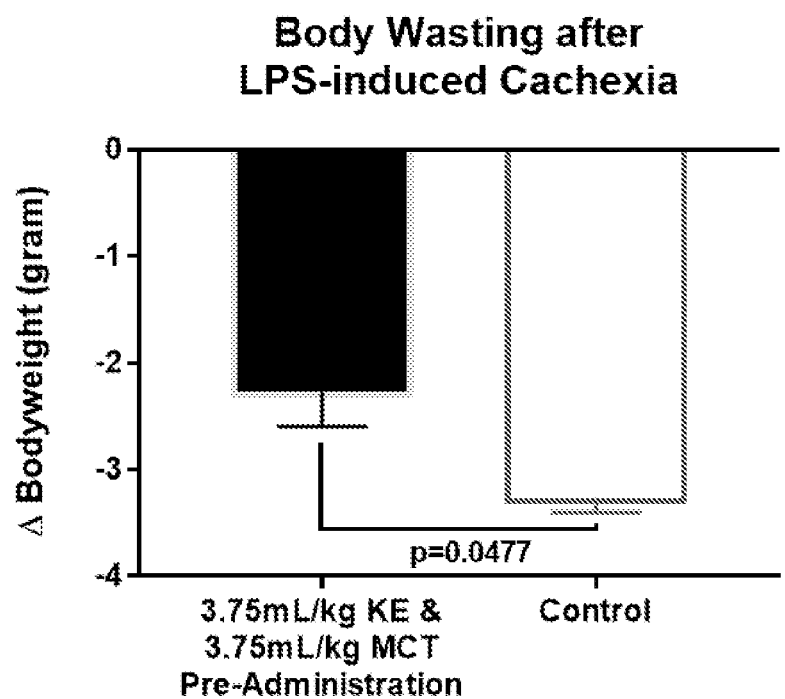
FIG. 2A depicts bodyweight change that accompanies Lipopolysaccharide after treatment with control or ketone supplementation in C57BL6J mice (p=0.0477).
Figure 2B:
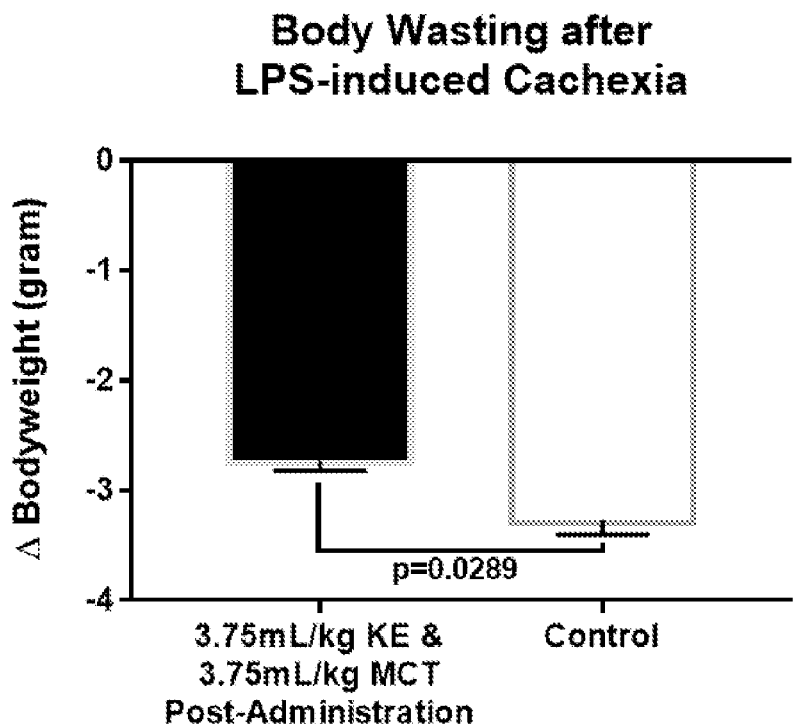
FIG. 2B depicts bodyweight change that accompanies Lipopolysaccharide after treatment with control or ketone supplementation in C57BL6J mice (p=0.0289).

FIGS. 2A-2B depict results from an analysis of treatment of catabolic/cachexia/atrophy/wasting stimulus in form of lipopolysaccharide using R,S-1, 3-butanediol acetoacetate diester in combination with medium chain triglyceride (KE+MCT), as compared to control (n=3). Catabolism/cachexia/atrophy/wasting was induced by lipopolysaccharide (LPS). FIGS. 2A-2B depict results 1-day post LPS-induced cachexia, where subjects were treated KE+MCT, as compared to control which were not treated with KE+MCT. Data illustration significant reduction in wasting with both pre and post administration of KE & MCT formulation treatment compared to controls.

Example 4

Figure 3A:
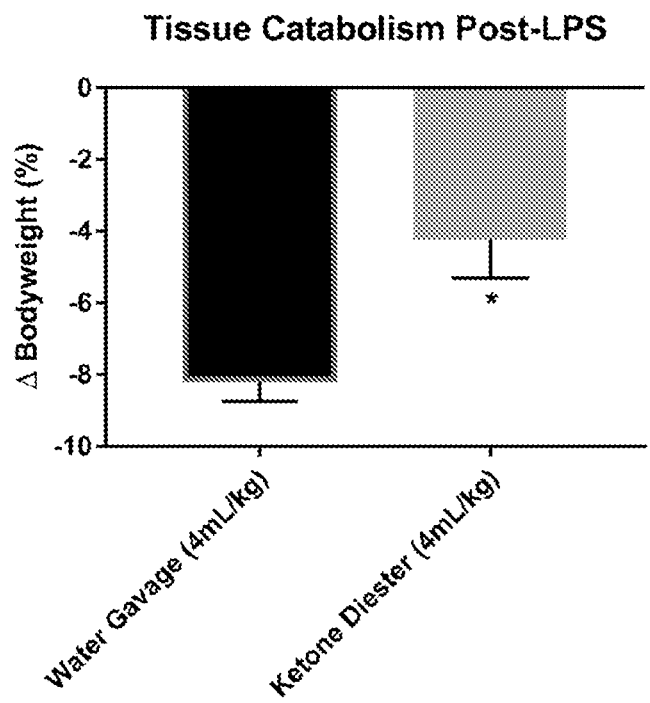
FIG. 3A depicts acute percent bodyweight changes that accompany Lipopolysaccharide after treatment with control or ketone supplementation in VM/Dk mice.
Figure 3B:
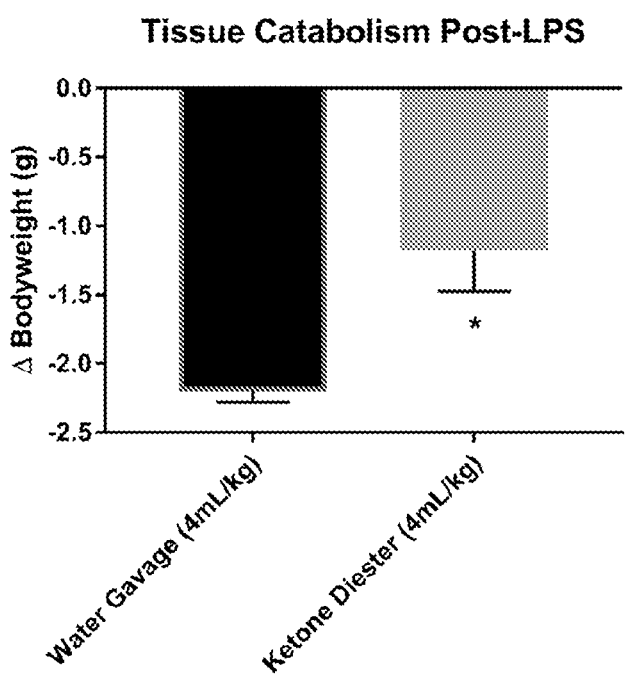
FIG. 3B depicts acute bodyweight changes that accompany Lipopolysaccharide after treatment with control or ketone supplementation in VM/Dk mice.
Figure 3C:
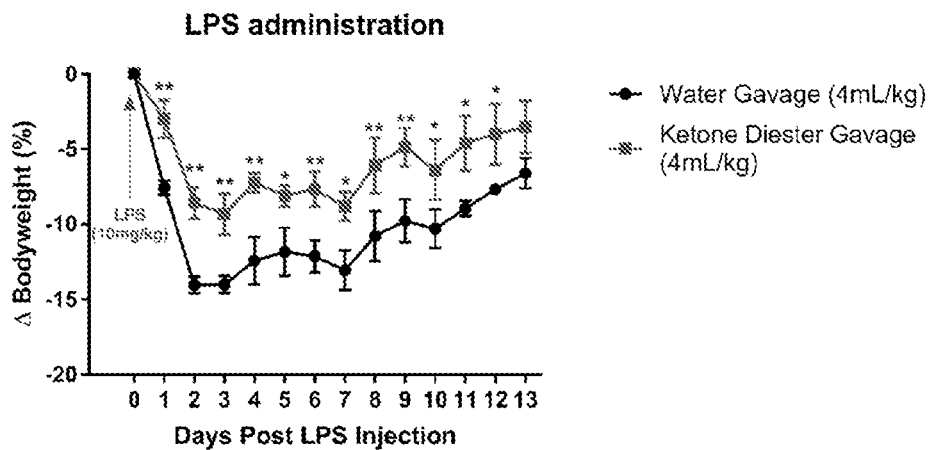
FIG. 3C depicts chronic percent bodyweight changes that accompany Lipopolysaccharide after treatment with control or ketone supplementation in VM/Dk mice.
Figure 3D:
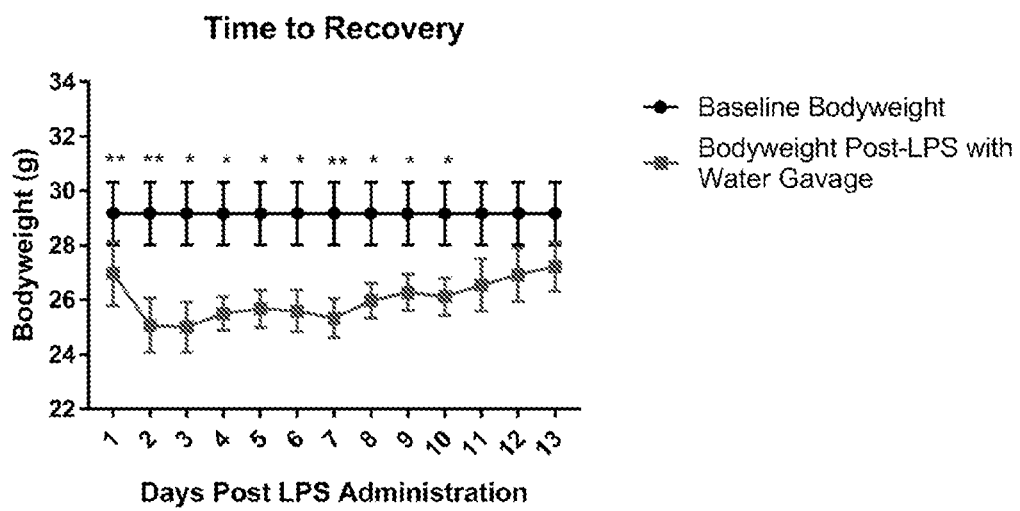
FIG. 3D depicts the difference in bodyweight with control treatment at baseline versus each day following Lipopolysaccharide treatment.
Figure 3E:
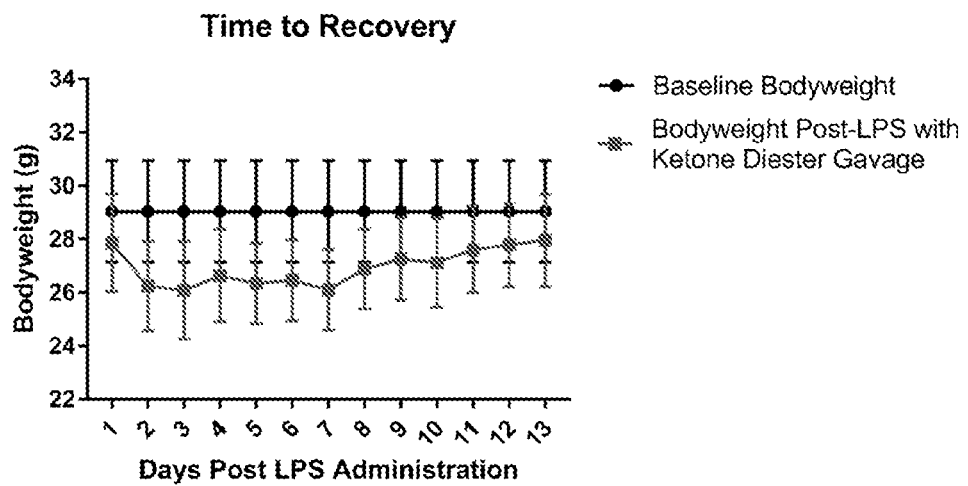
FIG. 3E depicts the difference in bodyweight with ketone supplement treatment at baseline versus each day following Lipopolysaccharide treatment.

FIGS. 3A-E depict results from Weight matched animals who were administered 10 mg/kg LPS intraperitoneally. After intraperitoneal LPS injection, 4 mL/kg of water (n=4) or R/S 1,3 Butanediol Acetoacetate Diester (Ketone Diester; n=5) were intragastrically gavaged into animals one time. Bodyweight and food intake were tracked for 2 weeks post LPS administration. FIG. 3A depicts Ketone Diester significantly attenuated tissue catabolism/atrophy/cachexia that is induced by LPS by 46% within the $1^{st}$ 24 hour post LPS administration. FIG. 3B depicts Ketone Diester significantly attenuated percentage of tissue catabolism/atrophy/cachexia that is induced by LPS by 48% within the $1^{st}$ 24 hours post LPS administration. FIG. 3C depicts Ketone Diester significantly attenuated tissue catabolism compared to control for multi-weeks post-LPS administrations. FIG. 3D-E depicts animals administered water gavage post LPS were not able to recovery to baseline bodyweight levels until 11 days post LPS administration. However, animals administered Ketone Diester did not significantly reduced in bodyweight post LPS administration. Together, FIG. 3A-E indicates that Ketone Diester is able to significantly attenuate catabolism/atrophy/cachexia that is induced by LPS administration acutely and chronically compared to control. Additionally, Ketone Diester is able to prevent any significant differences in tissue weight over time, while it took control 11 days to fully recovery tissue loss indicating that Ketone Diester dramatically reduces time to recovery post catabolism/atrophy/cachexia.

Example 5

Figure 4A:
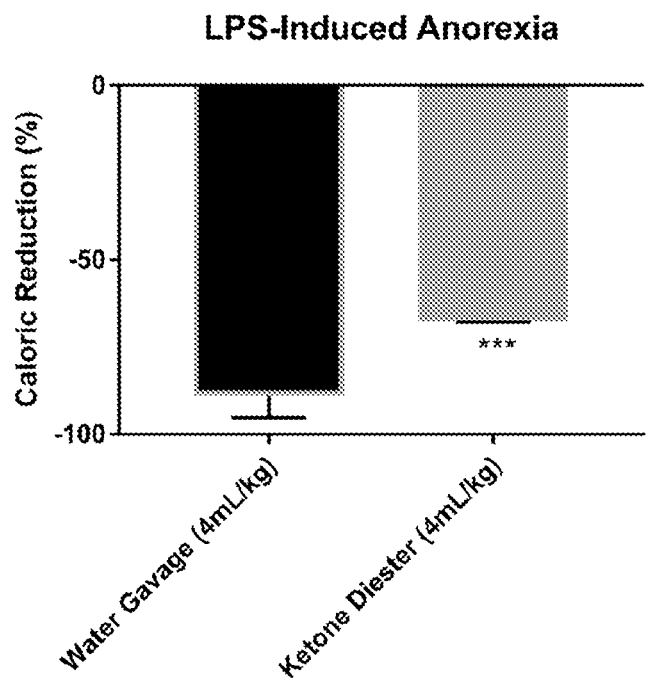
FIG. 4A depicts the difference in anorexia symptoms following Lipopolysaccharide administration with treatment with control or ketone supplementation.
Figure 4B:
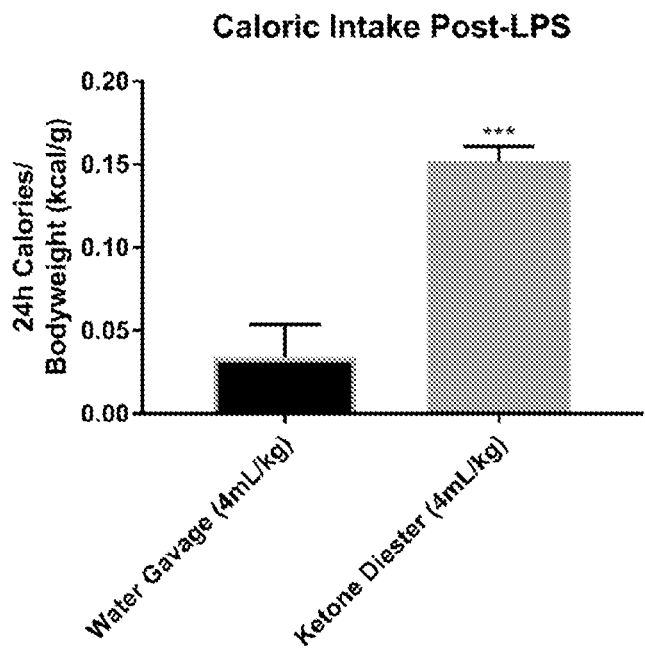
FIG. 4B depicts the difference in caloric intake following Lipopolysaccharide administration with treatment with control or ketone supplementation.

FIG. 4A-B depicts weight matched animals who were administered 10 mg/kg LPS intraperitoneally. After intraperitoneal LPS injection, 4 mL/kg of water (n=4) or R/S 1,3 Butanediol Acetoacetate Diester (Ketone Diester; n=5) were intragastrically gavaged into animals. Food Intake was tracted to determine if a one-time does of Ketone Diester was able to reduce anorexia experiences post catabolic/atrophy/cachexic stimulus (10 mg/kg LPS intraperitoneally). FIG. 4 A-B depict that Ketone Diester was able to significantly reduced the anorexia induced by catabolic/atrophy/cachexic stimulus. This indicates that Ketone Diester is able to significantly reduce overall symptom burden that accompanies catabolic/atrophy/cachexic stimulus.

Example 6

Figure 5A:
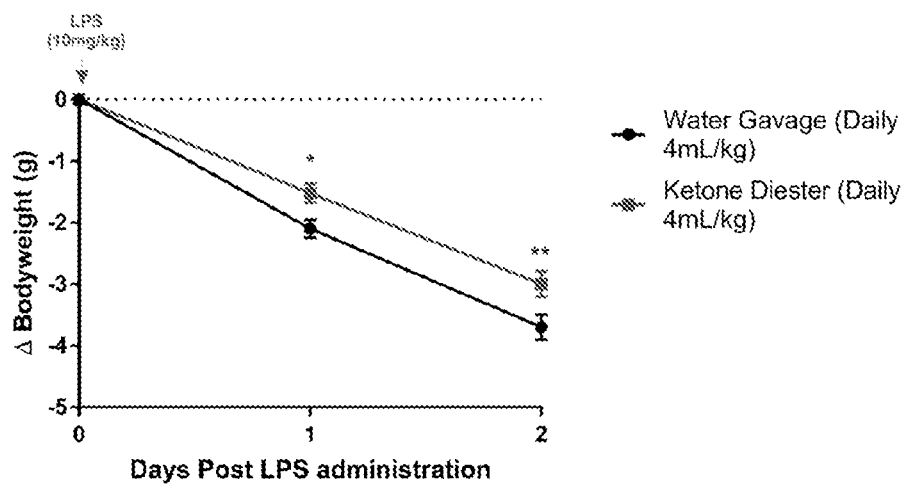
FIG. 5A depicts the difference in bodyweight following Lipopolysaccharide administration with multiple treatments with control or ketone supplementation with calories controlled across groups.
Figure 5B:
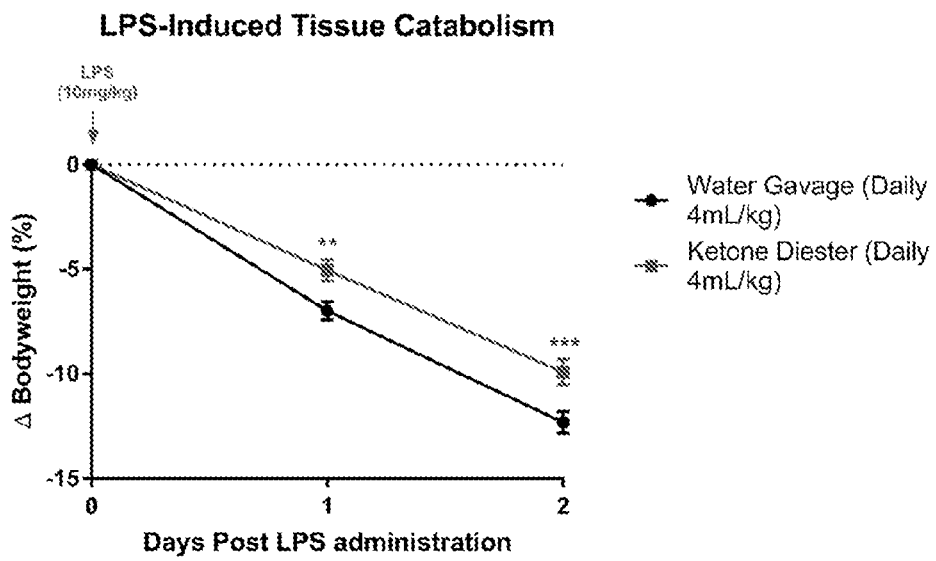
FIG. 5B depicts the difference in percent bodyweight following Lipopolysaccharide administration with multiple treatments with control or ketone supplementation with calories controlled across groups.

FIG. 5A-B depicts weight matched animals who were administered 10 mg/kg LPS intraperitoneally. After intraperitoneal LPS injection, 4 mL/kg of water (n=4) or R/S 1,3 Butanediol Acetoacetate Diester (Ketone Diester; n=4) were intragastrically gavaged into animals. Animals were pair fed to ensure calories were equivalent between groups to remove influence of caloric intake on tissue catabolism/atrophy/cachexia. FIG. 5A-B show that the Ketone Diester significantly attenuated tissue catabolism/atrophy/cachexia that is induced by LPS. This effect was retained for a minimum of 2 days following catabolic/atrophy/cachexia stimulus (10 mg/kg LPS intraperitoneal). The ability of Ketone Diester to attenuate catabolism was independent of caloric intake/anorexia induced by LPS. Data indicates that multiple administrations of Ketone Diester is able to significantly reduced the catabolic response induced by a catabolic/atrophy/cachexic stimulus acutely and multi-days post catabolic/atrophy/cachexia stimulus independent of whether calorie intake between groups. This data combined with Prior experiments indicate that Ketone Diester works through multiple mechanisms to attenuate catabolic/atrophy/cachexia tissue wasting and overall disease/illness burden providing a robust anticatabolic agent.

Example 7

Figure 6A:
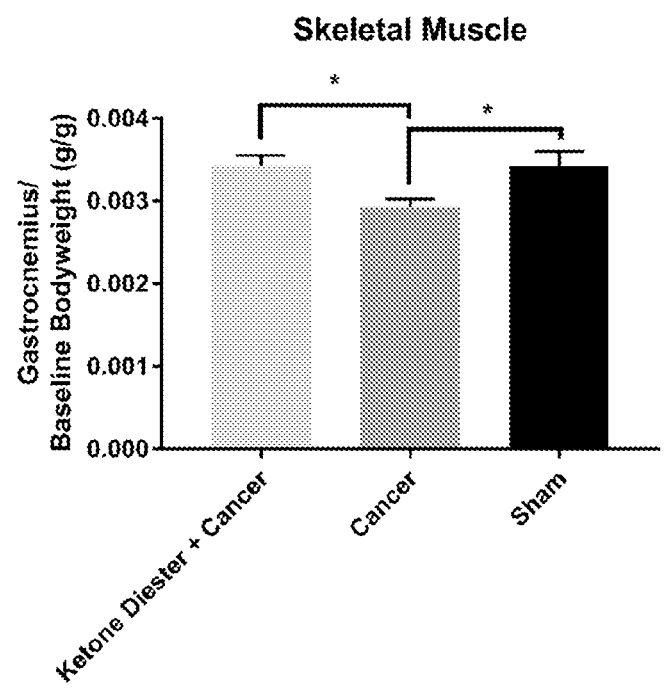
FIG. 6A depicts the difference in skeletal muscle weight following cancer cachexia administration (VM-M3) with control or ketone supplementation.
Figure 6B:
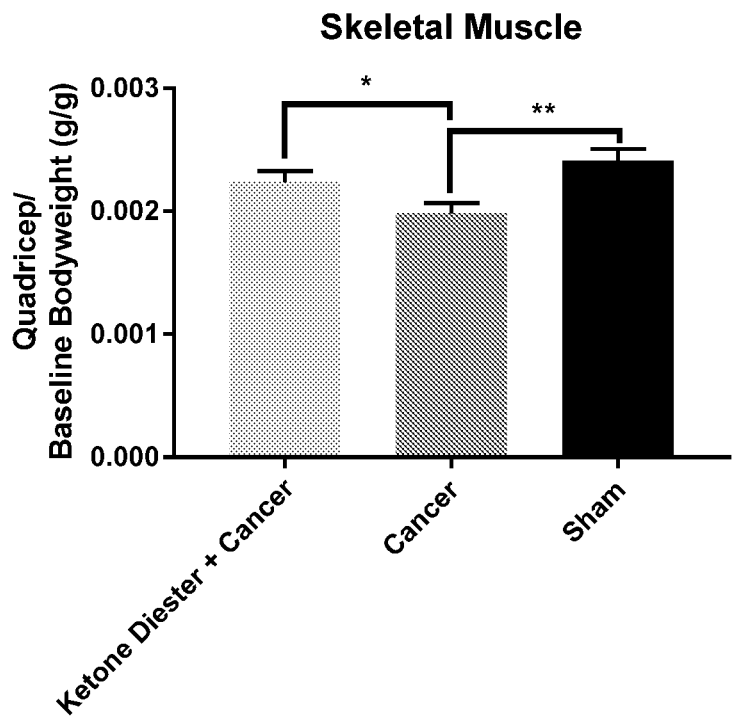
FIG. 6B depicts the difference in skeletal muscle weight following cancer cachexia administration (VM-M3) with control or ketone supplementation.

FIG. 6A-B depict weight matched animals who were split into 3 groups 1) Animals without cancer injected with vehicle on standard diet (Sham; n=11), 2) animals with cancer on standard diet (n=11), and 3) animals with cancer with ketone diester incorporated into the standard diet food at 30% by weight (n=11). Animals bodyweight was measured at baseline. Cancer groups were assessed in a validated model of cancer cachexia. At 21 days post vehicle or cancer injection, tissue were harvest and weighed. Skeletal Muscle weight was set as a ratio to baseline bodyweight to determine the differences in skeletal muscle tissue as compared to set pre-cancer timepoint. FIG. 6A-B show that Ketone Diester significantly attenuated both Gastrocnemius and Quadricep catabolism/atrophy/cachexia that is induced by LPS. This data indicates that incorporating the Ketone Diester into the diet significantly reduced the catabolic response induced by a catabolic/atrophy/cachexic stimulus (cancer cachexia).

Example 8

Figure 7A:
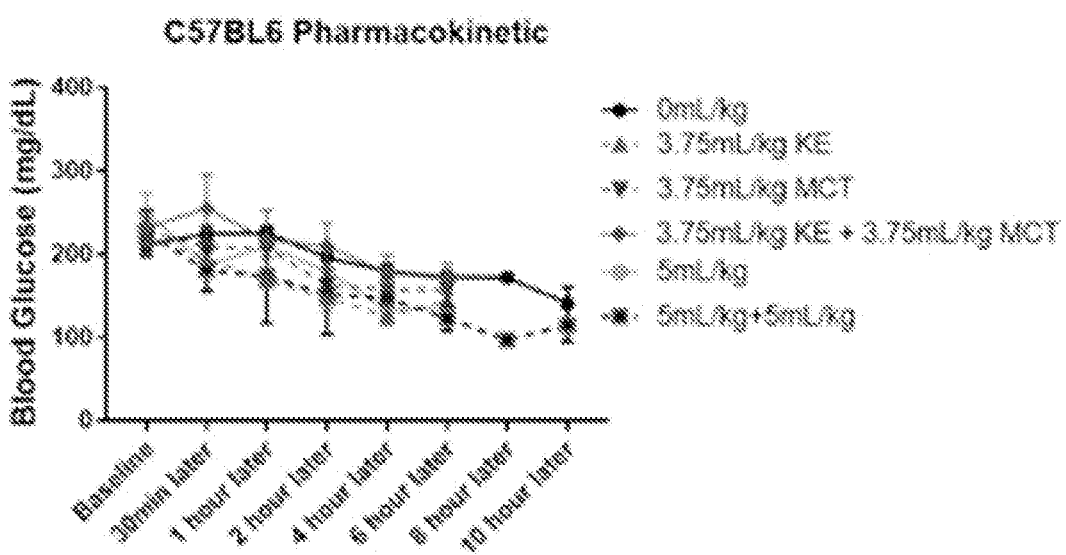
FIG. 7A depicts blood glucose pharmacokinetics of a novel R/S 1,3 Butanediol Acetoacetate Diester+MCT formulation in C57BL6 mice.
Figure 7B:
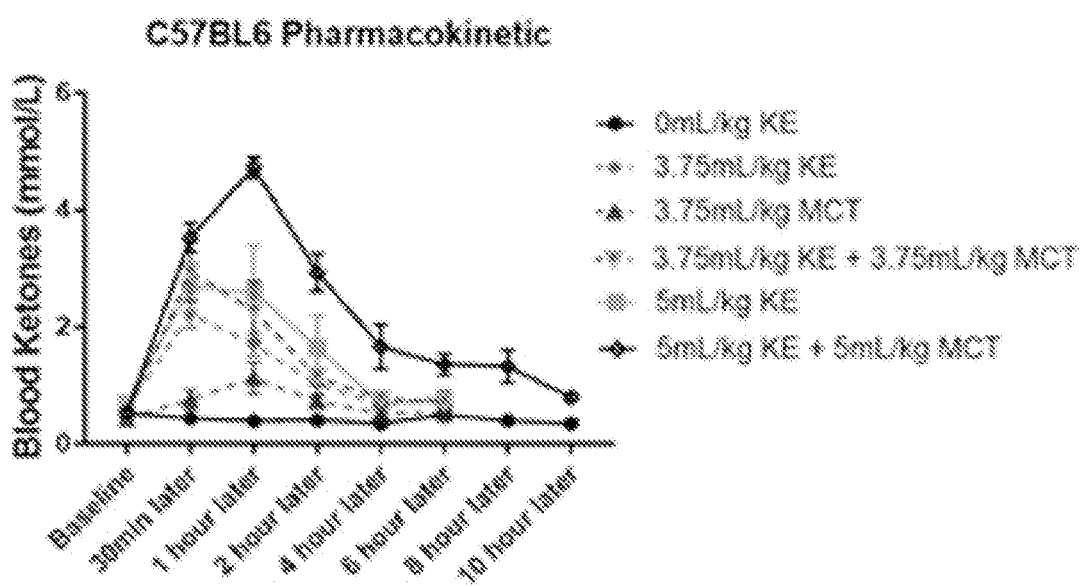
FIG. 7B depicts blood ketone pharmacokinetics of a novel R/S 1,3 Butanediol Acetoacetate Diester+MCT formulation in C57BL6 mice.

FIG. 7A-B depict blood glucose and blood ketone pharmacokinetics novel R,S-1, 3-butanediol acetoacetate diester in combination with medium chain triglyceride (KE+MCT) ketone formulation administered at various dosages. Data illustrations novel blood metabolite changes over a 10 hour period in blood glucose and blood ketones following administration of KE+MCT compared to KE, MCT, or water control alone.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of treating muscle wasting resulting from a disorder in a patient in need thereof, comprising administering a therapeutically effective amount of a R,S 1,3 butanediol diacetoacetate to the patient, wherein the disorder is cancer cachexia, sepsis, or anorexia.

2. The method of claim 1, further comprising administering a medium chain triglyceride.

3. The method of claim 1, wherein the disorder is cancer cachexia or sepsis.

4. The method of claim 1, wherein the disorder is anorexia, fasting.

5. The method of claim 1, wherein R,S 1,3 butanediol diacetoacetate is administered with glucose, fructose, sucralose, galactose, vitamins, minerals, proteins, essential amino acids, or any combination thereof.

6. The method of claim 1, wherein the patient is on a standard diet.

7. The method of claim 1, further comprising administering one or more Vitamin A, Vitamin B6, Vitamin B12, Vitamin C, Vitamin D, Vitamin E, potassium, calcium, magnesium, chromium, selenium, proteins, essential amino acids, and branch chain amino acids.

* * * * *